United States Patent [19]

Otsu et al.

[11] Patent Number: 4,822,924

[45] Date of Patent: Apr. 18, 1989

[54] PROCESS FOR PRODUCING 2,6-DICHLOROBENZYL ALCOHOL

[75] Inventors: Ichiro Otsu; Sueo Kanno; Sinichi Sato; Tetsuya Kondo, all of Koriyama, Japan

[73] Assignee: Hodogaya Chemical Co., Ltd., Tokyo, Japan

[21] Appl. No.: 137,086

[22] Filed: Dec. 23, 1987

[30] Foreign Application Priority Data

Dec. 27, 1986 [JP]  Japan ................................ 61-309114

[51] Int. Cl.$^4$ ..................... C07C 33/46; C07C 29/09
[52] U.S. Cl. ................................... 568/812; 568/715; 568/811
[58] Field of Search ..................... 568/812, 811, 715,

[56] References Cited

U.S. PATENT DOCUMENTS

| | | | |
|---|---|---|---|
| 2,939,886 | 6/1960 | Pritchard et al. | 568/811 |
| 3,993,699 | 11/1976 | Maeda et al. | 568/715 |
| 4,387,253 | 6/1983 | Gower | 568/812 |

*Primary Examiner*—Warren B. Lone
*Attorney, Agent, or Firm*—Oblon, Fisher, Spivak, McClelland & Maier

[57] ABSTRACT

A process for producing 2,6-dichlorobenzyl alcohol, which comprises reacting 2,6-dichlorobenzyl chloride with an acetate-forming agent to form its acetate, followed by hydrolysis to obtain 2,6-dichlorobenzyl alcohol, wherein anhydrous sodium acetate is used as the acetate-forming agent, and a quaternary ammonium salt is added as a phase transfer catalyst during the acetate-forming reaction.

5 Claims, No Drawings

PROCESS FOR PRODUCING 2,6-DICHLOROBENZYL ALCOHOL

The present invention relates to a process for producing 2,6-dichlorobenzyl alcohol (hereinafter referred to simply as 2,6-DCBAL). More particularly, it relates to an industrially advantageous process whereby 2,6-DCBAL can be produced in good yield. 2,6-DCBAL is useful as an intermediate for agricultural chemicals, medicines and dyestuffs.

Heretofore, the following methods are known for the production of substituted or unsubstituted benzyl alcohols from benzyl halides such as benzyl chloride or substitued benzyl halides such as o-chlorobenzyl chloride:

(1) A method wherein a benzyl halide is hydrolyzed with a dilute alkali metal hydroxide aqueous solution and an aqueous carbonate solution (Ullmann, vol. 4, p. 30).

(2) A method wherein a benzyl halide is reacted with e.g. sodium acetate or potassium acetate, and benzyl acetate thus obtained is hydrolyzed to obtain benzyl alcohol (U.S. Pat. Nos. 2,939,886 and 3,993,699).

(3) A method wherein a benzyl halide is reacted with sodium formate or potassium formate by using a tertiary amine or a quaternary ammonium salt as a catalyst, followed by ester exchange with an alcohol in the presence of an ester exchange catalyst to free benzyl alcohol (Japanese Unexamined Patent Publication No. 98729/1979).

(4) A method wherein a benzyl halide is hydrolyzed with an aqueous sulfuric acid solution (Rev. Roum. Chim. 1974, 19(7) 1221).

However, little has been reported on the synthesis of 2,6-DCBAL. In the above literature (4), it is reported only that a mixture comprising 2,6-dichlorobenzyl chloride (hereinafter referred to simply as 2,6-DCBC), 2,6-dichlorobenzal chloride and 2,6-dichlorobenzotrichloride, can be hydrolyzed by an aqueous sulfuric acid solution.

If the above methods (1) to (4) are employed for the production of 2,6-DCBAL, the following drawbacks will be brought about.

Firstly, in the case of the method (1), a dibenzyl ether product is produced in a substantial amount by a side reaction, whereby the yield of desired 2,6-DCBAL will be so low that the method is not practical. In the method (2), the reaction rate of the acetate is slow, and a long period of time is required to the completion of the reaction. It is conceivable to employ a large amount of a solvent to overcome this problem, but such a method is not industrially advantageous. The method (3) has a drawback that expensive sodium formate is employed. The method (4) is intended for the hydrolysis of 2,6-dichlorobenzal chloride, and such a method is not suitable fo the hydrolysis of 2,6-DCBC.

Thus, in the case of 2,6-DCBAL, it is difficult to apply methods useful for the production of other substituted or unsubstituted benzyl alcohols, probably due to the steric hindrance by the 2,6-dichloro substituents.

Under these circumstances, the present inventors have conducted extensive research for a process for producing highly pure 2,6-DCBAL from 2,6-DCBC industrially advantageously, and as a result, have found an extremely effective catalyst for the acetate-forming reaction of the 2,6-DCBC with anhydrous sodium acetate. The present invention has been accomplished on the basis of this discovery.

Namely, the present invention provides an industrially advantageous process for producing 2,6-DCBAL, wherein 2,6-DCBC is reacted with anhydrous sodium acetate in the presence of a quaternary ammonium salt as a phase transfer catalyst to form 2,6-dichlorobenzyl acetate (hereinafter referred to simply as 2,6-DCBAC), and 2,6-DCBAC is hydrolyzed to obtain 2,6-DCBAL.

Now, the present invention will be described in detail with reference to the preferred embodiments.

The quaternary ammonium salt used in the present invention may be any quaternary ammonium salt obtainable by the quaternary-conversion of a tertiary amine with an alkyl halide or a benzyl halide. Suitable quaternary ammonium salts include butylpyridinium bromide (BPB), benzyltriethylammonium bromide (BTEAB), benzyltriethylammonium chloride (BTEAC), benzyltrimethylammonium chloride (BTMAC), benzyltrimethylammonium fluoride (BTMAF), hexadecyltriethylammonium bromide (CTEAB), hexadecyltrimethylammonium bromide (CTMAB), hexadecyltrimethylammonium chloride (CTMAC), dibutyldimethylammonium chloride (DBDMA), decyltriethylammonium bromide (DTEAB), heptylpyridinium bromide (HPB), hexyltriethylammonium bromide (HTEAB), dodecylpyridinium bromide (LPB), dodecyltriethylammonium bromide (LTEAB), methyltrinonylammonium chloride (MTNAC), methyltriphenylammonium bromide (MTPAB) octyltriethylammonium bromide (OTEAB), tetrabutylammonium cyanide (TBA cyanide), tetrabutylammonium bromide (TBAB), tetrabutylammonium chloride (TBAC), tetrabutylammonium iodide (TBAI), tetrabutylammonium hydroxide (TBAOH), tetraethylammonium chloride (TEAC), tetramethylammonium bromide (TMAB), trioctylmethylammonium chloride (TOMAC), trioctylpropylammonium chloride (TOPAC) and tetrapropylammonium bromide (TPAB).

There is no particular restriction as to the amount of the quaternary ammonium salt to be used. It is usually used in an amount of from 0.01 to 5% by weight, preferably from 0.05 to 1% by weight, relative to 2,6-DCBC.

Sodium acetate to be used in the present invention is required to be anhydrous. However, inexpensive trihydrate may be employed by subjecting it to a dehydration operation such as azeotropic distillation to obtain anhydrous sodium acetate in the reaction system.

Sodium acetate react with 2,6-DCBC stoichiometrically, and it is usually used in at least stoichiometric amount required for the complete progress of the reaction. However, it is preferably used in a slightly excess amount of from 1.01 to 1.10 mols per mol of 2,6-DCBC.

The acetate-forming reaction is usually conducted within a temperature range of from 60° to 200° C., preferably from 80° to 100° C. The reaction pressure may range from reduced presure to high pressure. However, the reaction is preferably conducted under atmospheric pressure.

In the acetate-forming reaction, a solvent is not necessarily required. However, if necessary, the reaction may be conducted by using a solvent inert to the reaction, such as toluene, o-chlorotoluene, p-chlorotoluene, monochlorobenzene or dioxane. After the completion of the acetate-forming reaction, 2,6-DCBAC may be isolated from the reaction solution in high purity by such treatment as washing with water, followed by a conventional operation such as distillation or recrystallization. However, usually, the reaction solution is directly subjected to hydrolysis to obtain desired 2,6-DCBAL.

For the hydrolysis, a conventional alkali hydrolysis may be employed. Namely, an aqueous sodium hydroxide solution is added to the acetate reaction solution directly or after removal of the remaining sodium acetate by washing with water, and the mixture is heated to a temperature of from 80° to 110° C., whereby 2,6-DCBAL can readily be obtained.

The isolation of desired 2,6-DCBAL from the reaction solution after the hydrolysis can readily be conducted by a conventional technique such as distillation or recrystallization.

Thus, according to the process of the present invention, 2,6-DCBAC can be obtained from 2,6-DCBC in such a short period of time in such a high purity and in such a high yield as have been hardly possible to accomplish by conventional methods, and by further subjecting it to hydrolysis, desired 2,6-DCBAL can readily be obtained in a high purity and in a high yield.

Now, the present invention will be described in further detail with reference to Examples. However, it should be understood that the present invention is by no means restricted to such specific Examples.

EXAMPLE 1

Into a 500 ml four-necked flask equipped with a reflux condenser, a thermometer and a stirrer, 97.7 g (0.5 mol) of 2,6-DCBC, 45.1 g (0.55 mol) of anhydrous sodium acetate and 0.5 g of tetrabutylammonium chloride (TBAC) as a phase transfer catalyst, were charged, and the acetate-forming reaction was conducted at 100° C. for 2 hours. After the completion of the reaction, the reaction mixture was analyzed by gas chromatography, whereby the production rate of desired 2,6-DCBAC was found to be 99.5%.

Then, to the reaction mixture, 100 ml of water and 100 ml of toluene were added, and the mixture was stirred for 5 minutes for washing. Then, the aqueous layer was separated and removed. Then, 100 g (0.5 mol) of a 20% sodium hydroxide aqueous solution was added to the toluene layer, and the mixture was stirred at 95° C. for 1 hour. Then, the mixture was washed three times with 150 ml of warm water of 40° C. Then, the toluene layer was concentrated by an evaporator, and the residue was recrystallized from methanol to obtain 5.2 g of desired 2,6-DCBAL. The yield from 2,6-DCBC was 96.3%. The melting point of the product was from 96.7° to 98.1° C. As a result of the gas chromatography analysis, the purity was 99.8%.

COMPARATIVE EXAMPLE 1

In the same manner as in Example 1, the acetate-forming reaction and the hydrolysis were conducted without adding the phase transfer catalyst. The results are shown in Table 1.

EXAMPLES 2 to 13

In the same manner as in Example 1, the acetate-forming reaction and the hydrolysis were conducted by changing the type of the phase transfer catalyst. The results are shown in Table 1.

TABLE 1

| | Type of phase transfer catalyst | 2,6-DCBAC Production rate | 2,6-DCBAL Yield | Purity | Melting point |
|---|---|---|---|---|---|
| Comparative Example 1 | Nil | 14.2% | 12.3% | 98.2% | 90–94° C. |
| Example 2 | TOMAC | 99.4 | 95.8 | 99.8 | 96.7–98.0 |
| Example 3 | BTEAC | 98.9 | 93.5 | 99.7 | 96.5–97.7 |
| Example 4 | BTEAB | 98.4 | 92.9 | 99.7 | 96.5–97.9 |
| Example 5 | BTMAC | 98.9 | 93.4 | 99.8 | 96.4–97.9 |
| Example 6 | HPB | 94.2 | 89.1 | 99.6 | 96.3–97.1 |
| Example 7 | CTMAB | 97.9 | 92.8 | 99.4 | 96.0–96.9 |
| Example 8 | CTMAC | 99.3 | 95.6 | 99.8 | 96.6–98.1 |
| Example 9 | HTEAB | 99.2 | 95.7 | 99.8 | 96.7–97.9 |
| Example 10 | OTEAB | 99.1 | 95.8 | 99.7 | 96.5–97.8 |
| Example 11 | TBAI | 97.2 | 91.6 | 99.8 | 96.6–98.0 |
| Example 12 | TBAOH | 96.4 | 90.1 | 99.7 | 96.5–97.8 |
| Example 13 | TEAC | 99.0 | 93.5 | 99.8 | 96.7–98.1 |

COMPARATIVE EXAMPLE 2

In the same manner as in Example 1, the reaction was conducted by adding 0.5 g of triethylamine instead of using the phase transfer catalyst. As a result, the production rate of 2,6-DCBAC was 48.2%, and the yield of 2,6-DCBAL was as low as 41.6%.

COMPARATIVE EXAMPLE 3

In the same manner as in Example 1, the reaction was conducted by using 74.8 g (0.55 mol) of sodium acetate tri-hydrate instead of anhydrous sodium acetate. As a result, the production rate of 2,6-DCBAC was 36.4%, and the yield of 2,6-DCBAL was as low as 32.4%.

EXAMPLE 14

In the same manner as in Example 1, the acetate-forming reaction and the hydrolysis were conducted except that 74.8 g (0.05 mol) of sodium acetate tri-hydrate was used instead of anhydrous sodium acetate and before the acetate-forming reaction, 200 ml of toluene was added and azeotropic dehydration with toluene was conducted. As a result, the production rate of 2,6-DCBAC was 93.9%, the yield of 2,6-DCBAL was 92.5%, and the purity was 99.5%.

EXAMPLE 15

In the same manner as in Example 1, the reaction was conducted by adding 100 ml of toluene for the acetate-forming reaction. As a result, the production rate of 2,6-DCBAC was 99.0%, the yield of 2,6-DCBAL was 95.1%, and the purity was 99.6%.

We claim:

1. A process for producing 2,6-dichlorobenzyl alcohol, which comprises reacting 2,6-dichlorobenzyl chloride with an acetate-forming agent to form its acetate, wherein anhydrous sodium acetate is used as the acetate-forming agent, and a quaternary ammonium salt is added as a phase transfer catalyst during the acetate-forming reaction, and hydrolyzing said acetate with a hydrolyzing agent to form 2,6-dichlorobenzyl alcohol.

2. The process according to claim 1, wherein the quaternary ammonium salt is used in an amount of from 0.01 to 5% by weight relative to 2,6-dichlorobenzyl chloride.

3. The process according to claim 1, wherein anhydrous sodium acetate is used in an amount of from 1.01 to 1.10 mols per mol of 2,6-dichlorobenzyl chloride.

4. The process according to claim 1, wherein the acetate-forming reaction is conducted at a temperature of from 60° to 200° C.

5. The process accoring to claim 1, wherein the quaternary ammonium salt is butylpyridinium bromide, benzyltriethylammonium bromide, benzyltriethylammonium chloride, benzyltrimethylammonium chloride, benzyltrimethylammonium fluoride, hexadecyltriethylammonium bromide, hexadecyltrimethylammonium bromide, hexadecyltrimethylammonium chloride, dibutyldimethylammonium chloride, decyltriethylammonium bromide, heptylpyridinium bromide, hexyltriethylammonium bromide, dodecylpyridinium bromide, dodecyltriethylammonium bromide, methyltrinonylammonium chloride, methyltriphenylammonium bromide, octyltriethylammonium bromide, tetrabutylammonium cyanide, tetrabutylammonium bromide, tetrabutylammonium chloride, tetrabutylammonium iodide, tetrabutylammonium hydroxide, tetraethylammonium chloride, tetramethylammonium bromide, trioctylmethylammonium chloride, trioctylpropylammonium chloride or tetrapropylammonium bromide.

* * * * *